United States Patent
Ikegami et al.

(10) Patent No.: US 9,834,517 B2
(45) Date of Patent: Dec. 5, 2017

(54) METHOD FOR PRODUCING HALOHYDANTOIN COMPOUND AND HALOHYDANTOIN COMPOUND

(71) Applicant: NIPPOH CHEMICALS CO., LTD., Tokyo (JP)

(72) Inventors: Tomohiro Ikegami, Isumi (JP); Yukihiko Hanamura, Isumi (JP); Kazuhisa Inoue, Isumi (JP)

(73) Assignee: NIPPOH CHEMICALS CO., LTD., Tokyo (JP)

( * ) Notice: Subject to any disclaimer, the term of this patent is extended or adjusted under 35 U.S.C. 154(b) by 0 days.

(21) Appl. No.: 14/350,098

(22) PCT Filed: Nov. 15, 2013

(86) PCT No.: PCT/JP2013/080916
§ 371 (c)(1),
(2) Date: May 26, 2015

(87) PCT Pub. No.: WO2014/097787
PCT Pub. Date: Jun. 26, 2014

(65) Prior Publication Data
US 2015/0344438 A1    Dec. 3, 2015

(30) Foreign Application Priority Data
Dec. 19, 2012   (JP) ................... 2012-277127

(51) Int. Cl.
*C07D 233/82*   (2006.01)
*C07D 233/72*   (2006.01)

(52) U.S. Cl.
CPC ......... *C07D 233/82* (2013.01); *C07D 233/72* (2013.01)

(58) Field of Classification Search
CPC ................. C07D 233/82; C07D 233/72
See application file for complete search history.

(56) References Cited

U.S. PATENT DOCUMENTS

| | | | |
|---|---|---|---|
| 2,392,505 A * | 1/1946 | Rogers .............. | C07D 233/82 548/101 |
| 2,795,556 A | 6/1957 | Quinn | |
| 4,012,565 A | 3/1977 | Freedman | |
| 4,100,348 A | 7/1978 | Habermeier | |
| 4,204,915 A | 5/1980 | Kurata et al. | |
| 4,745,189 A | 5/1988 | Lee et al. | |
| 5,780,641 A | 7/1998 | Yerushalmi et al. | |
| 5,953,456 A | 9/1999 | Ikeda et al. | |
| 7,897,785 B2 * | 3/2011 | Inoue ................ | C07D 233/82 548/320.5 |
| 2009/0259050 A1 | 10/2009 | Inoue et al. | |
| 2011/0087031 A1 | 4/2011 | Inoue et al. | |
| 2011/0092714 A1 | 4/2011 | Inoue et al. | |
| 2011/0144350 A1 | 6/2011 | Inoue et al. | |

FOREIGN PATENT DOCUMENTS

| | | |
|---|---|---|
| CN | 1788564 A | 6/2006 |
| CN | 102628644 A | 8/2012 |
| EP | 0785192 | 7/1997 |
| EP | 1939184 | 7/2008 |
| EP | 2937338 | 10/2015 |
| JP | 34-10025 | 11/1959 |
| JP | 53-116314 | 10/1978 |
| JP | 8-325192 | 12/1996 |
| JP | 09-316057 | 12/1997 |
| JP | 10-28529 | 2/1998 |
| JP | 2002-030072 | 1/2002 |
| JP | 2002-275008 | 9/2002 |
| JP | 2005-291598 | 10/2005 |
| WO | 02/08227 | 1/2002 |
| WO | 2007/026766 | 3/2007 |

OTHER PUBLICATIONS

Mullin, J. M. "Sublimation." Ullmann's Encyclopedia of Industrial Chemistry 2003, 34, 535-555.*
Orazi O. et al.,"N-Iodohydantoins, II. Iodinations with 1, 3-Diiodo-5, 5-dimethylhydantoin," J. Org. Chem., 1965, vol. 30, p. 1101-1104
Sigma Aldrich Corp., Aldrich Chemistry, Handbook of Fine Chemicals, 2009-2010, 2009, p. 867.
International Search Report, International Patent Application No. PCT/JP2013/080916, mailed Dec. 17, 2013.
International Preliminary Report on Patentability, International Patent Application No. PCT/JP2013/080916, mailed Jul. 2, 2015.
CN Office Action, CN Patent Application No. 201380062930.3 mailed Mar. 23, 2016, English translation provided.
European Search Report, EP Patent Application No. 13864539.5 mailed Apr. 1, 2016.
European Search Report, EP Patent Application No. 13864692.2, mailed Apr. 6, 2016.
Office Action, U.S. Appl. No. 14/350,097, mailed Mar. 7, 2017.
International Preliminary Report on Patentability in corresponding PCT/JP2006/317113, mailed Sep. 9, 2008.
Decision of the technical board of appeal for EP patent application No. 93106005.7, mailed Feb. 12, 1998.
Presentation of Publications and the Like and its notification for 2007-533295, mailed Jul. 9, 2010.
Office Action for CN application No. 200680031821.5, mailed Feb. 5, 2010.

(Continued)

*Primary Examiner* — Michael Barker
*Assistant Examiner* — Amanda L Aguirre
(74) *Attorney, Agent, or Firm* — Casimir Jones, SC

(57) ABSTRACT

A method for producing a halohydantoin compound according to the present invention includes the steps of: (a) providing, in a dryer, a composition containing (i) at least one component selected from the group consisting of water, an organic solvent, and elemental halogen and (ii) a halohydantoin compound; and (b) drying the composition under reduced pressure in the dryer, the reduced pressure being reduced to a pressure lower than atmospheric pressure while introducing an inert gas from an outside source into the dryer.

6 Claims, 1 Drawing Sheet

(56) References Cited

OTHER PUBLICATIONS

Office Action for CN application No. 200680031821.5, mailed Feb. 24, 2011.
European Search Report for 06797085.5, mailed Jun. 18, 2010.
Office Action for EP patent application No. 06797085.5, mailed Feb. 3, 2012.
Office Action for EP patent application No. 06797085.5, mailed Sep. 11, 2012.
European Search Report for EP patent application No. 12180060.1, mailed Sep. 28, 2012.
Office Action for EP patent application No. 12180060.1, mailed Jun. 12, 2013.
European Search Report for EP patent application No. 12180061.9, Oct. 2, 2012.
Office Action for EP patent application No. 12180061.9, mailed Sep. 18, 2013.
Summons to attend oral proceedings for EP patent application No. 12180061.9, mailed Apr. 11, 2014.
European Search Report for EP patent application No. 15154215.6, mailed Jun. 12, 2015.
Office Action for EP patent application No. 15154215.6, mailed Aug. 1, 2016.
Office Action for IN patent application No. 858/KOLNP/2008, mailed May 9, 2013.
Office Action for IN patent application No. 858/KOLNP/2008, mailed May 14, 2015.
Office Action for JP patent application No. 2007-533295, mailed Jun. 19, 2012.
Office Action for JP patent application No. 2012-180595, mailed Feb. 18, 2014.
Office Action for JP patent application No. 2012-180595, mailed Oct. 7, 2014.
Office Action for JP patent application No. 2014-266271, mailed Dec. 15, 2015.
Office Action for JP patent application No. 2014-266271, mailed Aug. 2, 2016.
Office Action for U.S. Appl. No. 11/991,285, mailed Aug. 26, 2009.
Office Action for U.S. Appl. No. 11/991,285, mailed Dec. 3, 2009.
Office Action for U.S. Appl. No. 11/991,285, mailed Jun. 7, 2010.
Office Action for U.S. Appl. No 12/926,900, mailed Feb. 15, 2013.
Office Action for U.S. Appl. No. 12/926,900, mailed Dec. 5, 2013.
Office Action for U.S. Appl. No. 12/926,899, mailed Jan. 31, 2012.
Office Action for U.S. Appl. No. 12/926,899, mailed Sep. 14, 2012.
Office Action for U.S. Appl. No. 12/926,899, mailed Jan. 30, 2013.
Office Action for U.S. Appl. No. 12/926,899, mailed Jun. 20, 2013.
Office Action for U.S. Appl. No. 12/926,898, mailed Feb. 14, 2013.
Office Action for U.S. Appl. No. 12/926,898, mailed Aug. 23, 2013.
Franks, Felix "Freeze-drying of bioproducts: putting principles into practice" (European Journal of Pharmaceuticals and Biopharmaceuticals, 45, (1998); p. 221-229)
Raab et al., "Carbon-14 Labelling of a Trifluolomethoxy Group: Synthesis of a Substance P Antagonist" J Labelled Cpd Radiopharm, 2001, vol. 44, pp. 815-829.
Harker, J.H. et al., Chapter16: "Drying", Chemical Engineering, Jan. 1, 2002, Elsevier Butterworth-Heinemann, XP002584711, ISBN:0750644451, vol. 2.
Japanese Industrial Standards Committee, JIS Handbook 49, Version 2004, Chemical Analysis, front page English language translation only, pp. 1-20.
Kouniaki et al. The effect of high hydrostatic pressure on anthocyanins and ascorbic acid in blackcurrants (*Ribes nigrum*) (Flavour. Fragr. J. 2004; 19: 281-286).
Aquabrome's Safety Data Sheet by Biolab (1-bromo-3-chloro-5,5-dimethylhydantoin—Jul. 2005), six pages.
Questions and Answers on USP 797. (May 5, 2007). Retrieved from http://www.usp797.org/QA-E9.htm—May 5, 2007, three pages, May 18, 2017.
Stahl et al. "The effect of process variables on the degradation and physical properties of spray dried insulin intended for inhalation" (Int. J. Pharm. (Feb. 21, 2002), 233(1-2); pp. 227-237).
Vapor Pressure. (Oct. 1999). Retrieved from http://hyperphysics.phy-astr.gsu.edu/hbase/kinetic/vappre.html—Vapor Pressure—Oct. 1999 pp. 1-4.
U.S. Restriction Requirement for U.S. Appl. No. 14/350,097, dated Sep. 22, 2016.
International Search Report of PCT/JP2013/080918, dated Dec. 17, 2013.
International preliminary report on patentability of PCT/JP2013/080918, dated Jul. 2, 2015.
EP Office Action for EP Patent Application No. 15154215.6, dated Mar. 28, 2017.
U.S. Office Action for U.S. Appl. No. 15/351,032, dated May 18, 2017.
Office Action for corresponding JP Patent Application No. 2014-553022, dated Aug. 8, 2017.
Shaoyun, Zhang, Inorganic chemistry, published May 31, 2008, p. 42.
Office Action for CN Patent Application No. 201380062897.4, dated Aug. 10, 2017, 13 total pages.
Hirata, Mitsuho, Distillation, Kagaku to Seibutsu, vol. 2 (1964), No. 6, pp. 31-36.
Office Action for JP Patent Application No. 2014-553023, dated Aug. 22, 2017, 18 total pages.

* cited by examiner

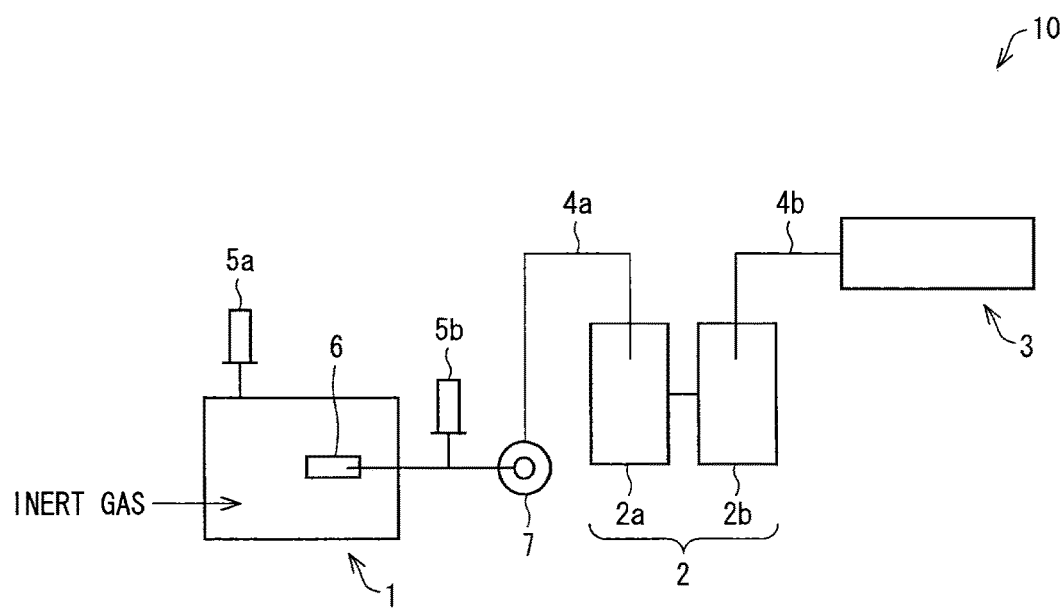

METHOD FOR PRODUCING HALOHYDANTOIN COMPOUND AND HALOHYDANTOIN COMPOUND

TECHNICAL FIELD

The present invention relates to a method for producing a halohydantoin compound and to a halohydantoin compound.

BACKGROUND ART

A halohydantoin compound has been widely used as a sensitizer for a photograph or the like or as a halogenating agent or an oxidizing agent for use in a process of producing a medicinal product, an agricultural chemical, a compound, or the like.

In particular, 1,3-diiodo-5,5-dimethylhydantoin is considered as a promising compound, as 1,3-diiodo-5,5-dimethylhydantoin is high in iodine content and an economical method for producing 1,3-diiodo-5,5-dimethylhydantoin has been disclosed.

As a method for producing 1,3-diiodo-5,5-dimethylhydantoin, for example, a method including the step of causing 5,5-dimethylhydantoin and iodine monochloride to react with each other in the presence of a base in a mixed solvent of an aqueous solution of a base and an organic solvent and a refining method have been disclosed (see, for example, Patent Literature 1 and Non Patent Literature 1).

Non Patent Literature 1 describes the following method: First, 5,5-dimethylhydantoin and iodine monochloride are reacted with each other with use of a sodium hydroxide aqueous solution and carbon tetrachloride. Next, the resulting crystals are washed with water, and are further washed with anhydrous ethyl acetate. After that, the crystals are dried at 60° C. under reduced pressure, whereby 1,3-diiodo-5,5-dimethylhydantoin is refined. Non Patent Literature 1 states that the resulting 1,3-diiodo-5,5-dimethylhydantoin is a reagent which can be preserved in a desiccator in a dark place without requiring a recrystallizing step.

Further, Patent Literature 1 gives the following description: First, 5,5-dimethylhydantoin and iodine monochloride are reacted with each other in a sodium hydroxide aqueous solution with use of N,N-dimethylformamide or an n-butyl acetate solvent. Next, the precipitated crystals as a result of the reaction are collected by filtration, and then dried under reduced pressure, thereby being refined.

CITATION LIST

Patent Literature 1

Japanese Patent Application Publication, Tokukai, No. 2002-30072 A (Publication Date: Jan. 29, 2002)

Non Patent Literature 1

ORFEO O. ORAZI., et al., N-Iodohydantoins. II. Iodinations with 1,3-Diiodo-5,5-dimethylhydantoin, *J. Org. Chem.*, 1965, Vol. 30, p. 1101-1104

SUMMARY OF INVENTION

Technical Problem

With the refining method described in Non Patent Literature 1, the yield of 1,3-diiodo-5,5-dimethylhydantoin is as low as 75%, and 1,3-diiodo-5,5-dimethylhydantoin contains 65% of effective iodine. Non Patent Literature 1 makes no mention of the purity of 1,3-diiodo-5,5-dimethylhydantoin.

Further, Patent Literature 1 makes no mention of the purity of 1,3-diiodo-5,5-dimethylhydantoin that is obtained by the refining method described therein.

The inventors of the present invention diligently studied the methods for refining a halohydantoin compound described in these literatures. As a result, the present inventors finally found the following problems:

A halohydantoin compound is so unstable at normal temperature that the halohydantoin compound needs to be refrigerated for preservation. Further, when suspended in water, a halohydantoin compound gradually decomposes to liberate iodine. Furthermore, when heated in the state of being a wet material containing a certain or lager amount of a mixed liquid component such as a mixture of water and an organic solvent, a halohydantoin compound is more unstable, so that the halohydantoin compound decomposes to liberate a hydantoin compound and elemental iodine. This undesirably causes a decrease in purity of the halohydantoin compound. Further, the elemental iodine thus liberated undesirably causes coloring of the halohydantoin compound and corrosion of refining equipment.

The present invention has been made in view of the foregoing problems, and it is an object of the present invention to provide a method for producing a halohydantoin compound by removing a component such as water from a composition containing the halohydantoin compound while inhibiting the halohydantoin compound from decomposing to invite coloring of the halohydantoin compound and corrosion of the equipment.

Solution to Problem

In order to solve the above problems, a method for producing a halohydantoin compound according to the present invention includes the steps of: (a) providing, in a dryer, a composition containing (i) at least one component selected from the group consisting of water, an organic solvent, and elemental halogen and (ii) a halohydantoin compound; and (b) drying the composition under reduced pressure in the dryer, the reduced pressure being reduced to a pressure lower than atmospheric pressure while introducing an inert gas from an outside source into the dryer.

A halohydantoin compound according to the present invention has a purity of not less than 98% by weight and contains not greater than 0.9% by mass of elemental halogen.

Advantageous Effects of Invention

The present invention brings about an effect of making it possible to remove a component such as water from a composition containing the halohydantoin compound while inhibiting the halohydantoin compound from decomposing to invite coloring of the halohydantoin compound and corrosion of the equipment.

BRIEF DESCRIPTION OF DRAWINGS

FIG. 1 is a diagram schematically showing a configuration of a production apparatus 10 that is an embodiment of a production apparatus for carrying out a production method according to the present invention.

DESCRIPTION OF EMBODIMENTS

A method for producing a halohydantoin compound according to the present invention includes the steps of: (a)

providing, in a dryer, a composition containing (i) at least one component selected from the group consisting of water, an organic solvent, and elemental halogen and (ii) a halohydantoin compound; and (b) drying the composition under reduced pressure in the dryer, the reduced pressure being reduced to a pressure lower than atmospheric pressure while introducing an inert gas from an outside source into the dryer. The component here is a substance that has a vapor pressure of not less than 35 Pa at 25° C.

An example of the composition (hereinafter referred to as "pre-dried composition" for convenience of explanation) containing (i) at least one component (hereinafter referred to as "impurity component" for convenience of explanation) selected from the group consisting of water, an organic solvent, and elemental halogen and (ii) a halohydantoin compound is a pre-refined halohydantoin compound that is obtained by a conventional publicly-known method. That is, since the pre-refined halohydantoin compound that is obtained by the conventional publicly-known method contains the aforementioned impurity component, a halohydantoin compound containing such an impurity is expressed as "composition" in this specification.

An example of the conventionally publicly-known method for producing a halohydantoin compound is to cause a hydantoin compound and elemental halogen to react with each other in the presence of a base in an aqueous solution. An example includes the successive steps of: preparing a hydantoin metal salt by causing a hydantoin compound and an alkali metal salt (NaOH or KOH) to react with each other; and causing the hydantoin metal salt to react with iodine monochloride (ICl) or iodine monobromide (IBr). This gives a wet material containing a halohydantoin compound, i.e., a composition that serves as an object of treatment in the present invention. It should be noted that all the halohydantoin compounds contained in the composition may be identical in composition or alternatively, plurality of types of compositions of the halohydantoin compounds may be mixedly present in the composition.

Of the impurity components, the organic solvent is a remnant of the organic solvent used in the production of the pre-dried composition. Specific examples of the organic solvent encompass an ester solvent, an aromatic solvent, an ether solvent, and a chlorine solvent, with their boiling points in the range of not lower than 30° C. to not higher than 200° C. These solvents may be used alone, or a mixture of plural types of these solvents may be used. These examples of solvents can be suitably removed by the production method according to the present invention.

Examples of the ester solvent encompass methyl acetate, ethyl acetate, propyl acetate, isopropyl acetate, butyl acetate, isobutyl acetate, sec-butyl acetate, tert-butyl acetate, pentyl acetate, hexyl acetate, methyl propionate, ethyl propionate, propyl propionate, butyl propionate, methyl butyrate, ethyl butyrate, propyl butyrate, and butyl butyrate.

Examples of the aromatic solvent encompass benzene, toluene, ethylbenzene, propyl benzene, cumene, butylbenzene, isobutyl benzene, sec-butyl benzene, tert-butyl benzene, o-xylene, m-xylene, p-xylene, mesitylene, 1,2,3-trimethyl benzene, 1,2,4-trimethyl benzene, o-cymene, m-cymene, and p-cymene.

Examples of the ether solvent encompass diethyl ether, dipropyl ether, isopropyl ether, methyl-tert-butyl ether, methyl cyclopentyl ether, dibutyl ether, anisole, ethyl phenyl ether, tetrahydrofuran, tetrahydropyran, and 1,4-dioxane.

Examples of the chlorine solvent encompass chloropropane, chlorobutane, chloropentane, chlorohexane, chloroheptane, chloro octane, dichloromethane, 1,2-dichloroethane, 1,2-dichloropropane, 1,3-dichloropropane, 2,2-dichloropropane, 1,2-dichlorobutane, 1,3-dichlorobutane, 1,4-dichlorobutane, chloroform, 1,1,1-trichloroethane, 1,1,2-trichloroethane, 1,1,1,2-tetrachloroethane, 1,1,2,2-tetrachloroethane, 1,2,3-trichloropropane, and carbon tetrachloride.

Of the impurity components, examples of the elemental halogen encompass an unreacted remnant of the elemental halogen contained in the raw material used in the production of the pre-dried composition and elemental halogen liberated from the halohydantoin compound once synthesized. Specific examples of the elemental halogen encompass iodine, bromine, and chlorine. These simple halogen elements may be used alone, or a mixture of plural types of these simple halogen elements may be used.

The dryer needs only be one which can contain the composition therein, which is configured to introduce an inert gas therein, and the pressure in which can be reduced to be lower than the atmospheric pressure. Suitably usable examples of the dryer encompass a rotary container vacuum dryer (conical vacuum dryer, conical dryer), a rotary drum vacuum dryer (drum vacuum dryer), a vacuum belt dryer, a tray vacuum dryer, a reduced pressure dryer, etc. Among them, the rotary container vacuum dryer (conical vacuum dryer) and the rotary drum vacuum dryer (drum vacuum dryer) are preferred because they can stir the contents, so that drying efficiency is improved and uneven drying and agglomeration are inhibited, and because they are compact apparatuses.

The inert gas needs only be inert with respect to a halohydantoin compound, and examples of the inert gas encompass air, nitrogen, helium, argon, carbon dioxide, etc. Among these, from a cost standpoint, air and nitrogen are preferred and nitrogen is most preferred.

In the production method according to the present invention, while the inert gas is introduced into the dryer, the pressure in the dryer is reduced to be lower than the atmospheric pressure. Therefore, the inert gas introduced into the dryer is discharged through an outlet that is different from an inlet through which it was introduced. At this point, the impurity component is discharged out of the dryer together with the inert gas. At this point, the temperature of the inert gas needs only be room temperature and it is not necessary to use heated gas, so that the decomposition of the halohydantoin compound can be inhibited. Such removal of the impurity component from the pre-dried composition allows the halohydantoin compound to be higher in purity, and coloring of the halohydantoin compound can be inhibited because of the low elemental halogen content. Furthermore, the halohydantoin compound can be dried while being inhibited from decomposing.

An amount of introduction of the inert gas needs only be an amount that makes it possible to reduce the pressure in the dryer so that the pressure in the dryer is lower than the atmospheric pressure. For example, a rate of introduction of the inert gas have a lower limit of more preferably not less than 0.01 mol % equivalent/min or even more preferably not less than 0.05 mol % equivalent/min and an upper limit of more preferably not greater than 5.0 mol % equivalents/min, even more preferably not greater than 2.5 mol % equivalents/min, or most preferably not greater than 1.0 mol % equivalent/min, with respect to a total molar quantity of the impurity component (total amount of one component selected from the group consisting of water, an organic solvent, and elemental halogen prior to the drying). With a rate of introduction of not less than 0.01 mol % equivalent/min, the impurity component can be efficiently discharged out of the dryer together with the inert gas. This brings about such an advantage of making it possible to shorten the drying time. With a rate of introduction of not greater than 5.0 mol % equivalents/min, there is such an advantage that scattering of the halohydantoin compound is prevented so that filter clogging can be inhibited.

Furthermore, a total amount of introduction of the inert gas has a lower limit of more preferably not less than 0.1 mol % equivalent or even more preferably not less than 0.5 mol % equivalent and an upper limit of more preferably not greater than 10.0 mol % equivalents, even more preferably not greater than 5.0 mol % equivalents, or most preferably not greater than 2.5 mol % equivalents, with respect to the total molar quantity of the impurity component. With a rate of introduction of not less than 0.1 mol % equivalent, the impurity component can be efficiently discharged out of the dryer together with the inert gas. This brings about such an advantage of making it possible to shorten the drying time. A rate of introduction of not greater than 10.0 mol % equivalents is preferred from the point of view of reducing the cost of the inert gas.

During the drying with the introduction of the inert gas, the temperature in the dryer is more preferably not lower than 15° C., even more preferably not lower than 30° C., or especially preferably not lower than 50° C. Further, the temperature in the dryer is more preferably not higher than 100° C. or even more preferably not higher than 80° C. With a temperature of not lower than 15° C., the impurity component is sufficiently vaporized, so that removal efficiency is improved. With a temperature of not greater than 100° C., the decomposition of the halohydantoin compound can be inhibited. It should be noted that the term "temperature in the dryer" means the temperature of a space in the dryer.

The drying with the introduction of the inert gas is usually carried out with a rise in temperature from room temperature (10° C. to 30° C.) to the preset drying temperature, and the rate of temperature rise to the preset temperature is preferably not less than 1° C./hour, more preferably not less than 5° C./hour, or even more preferably not less than 10° C./hour and more preferably not greater than 40° C./hour or even more preferably not greater than 30° C./hour. With a rate of temperature rise of not less than 5° C./hour, the drying time can be favorably shortened. Drying at a rate of temperature rise of not greater than 40° C./hour is preferable, because it is inhibited to form a large amount of agglomeration, which is formed with the aid of elemental iodine serving as a binder after being formed by the decomposition of part of the halohydantoin compound.

During the drying with the introduction of the inert gas, the pressure in the dryer for example has a lower limit of more preferably not less than 0.1 kPa or even more preferably 1.0 kPa and an upper limit of more preferably not greater than 50 kPa or even more preferably not greater than 40 kPa. With a pressure of not less than 0.1 kPa, the halohydantoin compound can be inhibited from rapidly drying, so that the particle size of the halohydantoin compound can be controlled as appropriate. With a pressure of not greater than 50 kPa, the impurity component is sufficiently vaporized, so that removal efficiency is improved. This makes it possible to inhibit the decomposition of the halohydantoin compound. In case of rapid drying under reduced pressure, the water and organic solvent contained in the halohydantoin compound are rapidly vaporized. This causes the particles of the halohydantoin compound to burst, so that the particle size becomes extremely small. Halohydantoin compound with an extremely small particle size is difficult to take out of the dryer and easy to scatter in filling as a product.

The method of the present invention for producing a halohydantoin compound is intended to produce, for example, a halohydantoin compound represented by the chemical formula I. The chemical formula I may have any combination of $R_1$, $R_2$, $X_1$, and $X_2$ within the after-mentioned range.

Specific preferable examples of the halohydantoin compound encompass 1-bromohydantoin, 1-iodohydantoin, 3-bromohydantoin, 3-iodohydantoin, 1,3-dibromohydantoin, 1,3-diiodo hydantoin, 1-bromo-5-methylhydantoin, 1-iodo-5-methylhydantoin, 3-bromo-5-methylhydantoin, 3-iodo-5-methylhydantoin, 1,3-dibromo-5-methylhydantoin, 1,3-diiodo-5-methylhydantoin, 1-bromo-5,5-dimethylhydantoin, 1-iodo-5,5-dimethylhydantoin, 3-bromo-5,5-dimethylhydantoin, 3-iodo-5,5-dimethylhydantoin, 1,3-dibromo-5,5-dimethylhydantoin, and 1,3-diiodo-5,5-dimethylhydantoin.

Any of these examples of halohydantoin compounds is suitably dried by the method of the present invention for producing a halohydantoin compound, so that the impurity component is removed. This makes it possible to obtain a halohydantoin compound having a water content of not greater than 3% by weight or preferably not greater than 2% by weight, having a purity of not less than 98% by weight, and containing not greater than 0.9% by mass of elemental halogen.

(Production Apparatus for Carrying Out a Production Method According to the Present Invention)

Next, an embodiment of a production apparatus for carrying out a production method according to the present invention is described with reference to a production apparatus 10 shown in FIG. 1. FIG. 1 is a diagram schematically showing a configuration of a production apparatus 10 that is an embodiment of a production apparatus according to the present invention.

First, the production apparatus 10 includes a dryer 1, a collection tank 2, and a pressure reducing pump 3.

The dryer 1 is a dryer for drying a composition (hereinafter referred to as "wet material") containing (i) at least one component selected from the group consisting of water, an organic solvent, and elemental halogen and (ii) a halohydantoin compound. The purity of the halohydantoin compound can be increased by removing a component except the halohydantoin compound by drying. For example, the drying is performed in such a way that while introducing an inert gas from an outside source into the dryer, pressure in the dryer 1 is reduced so that the pressure in the dryer 1 is lower than atmospheric pressure, and the wet material is dried while rotating the dryer 1. The dryer 1 includes a container in which the wet material is contained, and is configured such that the inside of the container can be heated with hot water running around the container. Further, the pressure in the dryer 1 is controlled by the pressure reducing pump 3 as will described later. It should be noted that a method for controlling the temperature and the pressure in the dryer 1 is not limited to the above method. Various dryers can be used as the dryer 1. For example, as mentioned above, a conical vacuum dryer can be used.

The dryer 1 is connected with the collection tank 2 via a duct 4a so that a gaseous component removed in the dryer 1 can be sent into the collection tank 2. Moreover, between the dryer 1 and an end of the duct 4a which end is connected to the dryer 1 (that is, a section connecting the dryer 1 and the duct 4a), a fabric filter (filtering means; usually made of fluororesin) 6 is provided so that gas (vaporized component) to be sent to the collection tank 2 is filtered. The presence of this filter 6 prevents (i) a solid substance scattered in the dryer 1 from causing blockage in a reduced pressure lines (ducts 4a and 4b) during drying and (ii) pollution or corrosion of the collection tank 2 or the pressure reducing pump 3, thereby consequently improving a collection rate of a target object.

The duct 4a is housed in a tubular pipe and heated by flow of the warm air through the pipe. This makes it possible to prevent a lump of iodine from blocking in the duct 4a. It should be noted that means for heating the duct 4a is not limited to the above configuration. Further, for the duct 4a, the production apparatus 10 is provided with manometers 5a and 5b for monitoring difference between the pressure in the dryer 1 and the pressure in the duct 4a, and a sight glass 7 for checking blockage in the duct 4a.

The collection tank 2 is a tank for collecting the component removed from the wet material. The collection tank 2 is connected with the duct 4a so that gas discharged from the dryer 1 is sent into the collection tank 2. One collection tank or a plurality of collection tanks may be provided as the collection tank(s) 2. In the present embodiment, two collection tanks (2a and 2b) are provided in series with each other. Specifically, the collection tank 2a is configured so that a space in the collection tank is empty and iodine contained in the gas sent in is collected in the collection tank 2a. Meanwhile, liquid for absorbing gas is contained in the collection tank 2b so that elemental halogen (i.e., bromine or chlorine) except iodine, water, an organic solvent and iodine that has not been collected in the collection tank 2a are collected in the collection tank 2b. As the liquid contained in the collection tank 2b, for example, a reducing-agent containing aqueous solution or an organic solvent can be employed. It should be noted that although, in the present embodiment, the space in the collection tank 2a is empty and liquid is contained in the collection tank 2b, liquid may be contained in the collection tank 2a. In this case, the production apparatus 10 may be configured to have only one collection tank, and elemental halogen except iodine, water, and an organic solvent are collected in the collection tank 2a. Further, the collection tank 2b may contain liquid, and the liquid may be circulated through the collection tank 2b by once taking the liquid out from the collection tank 2b and pouring the liquid like a shower back into the collection tank 2b. Alternatively, the collection tank 2a may contain liquid, and the liquid may be circulated through the collection tank 2a by once taking the liquid out from the collection tank 2a and pouring the liquid like a shower back into the collection tank 2a. As a further alternative, both the collection tanks 2a and 2b may contain liquid, and the liquid may be circulated through the collection tanks 2a and 2b by once taking the liquid out from the collection tanks 2a and 2b and pouring the liquid like a shower back into the collection tanks 2a and 2b.

The pressure reducing pump 3 is a pump for controlling the pressure in the dryer 1. The pressure reducing pump 3 is connected to the collection tank 2 via the duct 4b, so that the pressure reducing pump 3 reduces the pressure in the dryer 1 via the collection tank 2 and the ducts 4a and 4b. It should be noted that the reduced pressure in the dryer 1 is returned to an ordinary pressure, for example, with nitrogen.

It should be noted that the production apparatus for carrying out the production method of the present embodiment may be configured to include, for example, a control system. In this case, various types of processing in the production apparatus can be automated by use of the control system.

The present invention is not limited to the description of the embodiments above, but may be altered by a skilled person within the scope of the claims. An embodiment based on a proper combination of technical means disclosed in different embodiments is encompassed in the technical scope of the present invention.

According to the method of the present invention for producing a halohydantoin compound, as described above, it is preferable that a total amount of introduction of the inert gas be not less than 0.1 mol % equivalent and not greater than 10.0 mol % equivalent, with respect to a total molar quantity of one component selected from the group consisting of water, an organic solvent, and elemental halogen prior to the drying. Further, it is preferable that the rate of introduction of the inert gas be not less than 0.01 mol % equivalent/min and not greater than 5.0 mol % equivalent/min.

According to the method of the present invention for producing a halohydantoin compound, it is more preferable that the temperature in the dryer during the drying be not lower than 15° C. and not higher than 100° C.

According to the method of the present invention for producing a halohydantoin compound, it is more preferable that the pressure in the dryer during the drying be not lower than 0.1 kPa and not higher than 50 kPa.

The method of the present invention for producing a halohydantoin compound can be suitably applied to a composition in which the organic solvent is at least one selected from the group consisting of an ester solvent, an aromatic solvent, an ether solvent, and a chlorine solvent, each having a boiling point of not lower than 30° C. and not high than 200° C. under the atmospheric pressure.

The method of the present invention for producing a halohydantoin compound can be suitably applied to a composition in which the elemental halogen is at least one selected from the group consisting of iodine, bromine, and chlorine.

According to the method of the present invention for producing a halohydantoin compound, it is more preferable that the halohydantoin compound be a compound represented by chemical formula I:

[Chem. 1]

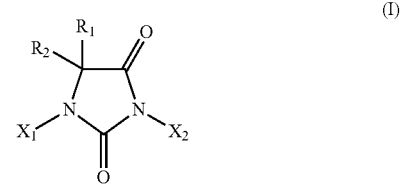

(I)

where
$R_1$ and $R_2$ are either identical to or different from each other, and are (i) each independently H, a substituted or unsubstituted C1 to C10 aliphatic hydrocarbon radical, a substituted or unsubstituted C3 to C10 alicyclic hydrocarbon radical, or a substituted or unsubstituted C6 to C10 allyl group or aralkyl group, more preferably H or a C1 to C8 aliphatic hydrocarbon radical, or even more preferably H or a methyl group, or (ii) most preferably both methyl groups; and $X_1$ and $X_2$ are either identical to or different from each other, and are (i) each independently H or a halogen atom, more preferably H, Br, or I, or even more preferably H or I, or (ii) most preferably both I, excluding a halohydantoin compound wherein $X_1$ and $X_2$ are both H.

EXAMPLES

The description below deals in greater detail with the embodiment of the present invention on the basis of Examples below. Needless to say, the present invention is not limited to the Examples below, and may take various embodiments in terms of details.

Quantitative determination of 1,3-diiodo-5,5-dimethylhydantoin was performed by a titration method with a 0.1 N aqueous solution of silver nitrate, and quantitative determination of butyl acetate was performed by an internal reference method of gas chromatography. Quantitative determination of elemental iodine extracted from a sample with use of chloroform was performed by colorimetry. The water content was measured by performing the quantitative determination of 1,3-diiodo-5,5-dimethylhydantoin, butyl acetate, and elemental iodine, confirming the absence of other impurities through NMR and gas chromatography, and subtracting the 1,3-diiodo-5,5-dimethylhydantoin and butyl acetate contents from the total weight of the composition containing 1,3-diiodo-5,5-dimethylhydantoin. This is because, although it is usual to measure a water content by using a Karl Fisher's apparatus, the present sample is reactive to a Karl Fisher's liquid and therefore its water content cannot be measured.

Experimental Example 1

Production of 1,3-diiodo-5,5-dimethylhydantoin

Water (74.4 kg) and 11.9% by weight of NaOH aqueous solution (17.3 kg) were fed into a 200-L glass lining reaction pot, and then 5,5-dimethylhydantoin (6.70 kg, 52.29 mol) was fed into the reaction pot. After that, the content of the reaction pot was cooled to 6° C.

Next, while a temperature of the content of the reaction pot was maintained at 0 to 7° C., an aqueous solution (14.10 kg, 4.19 mol) of 11.9% by weight of NaOH and a butyl acetate solution (35.84 kg, 92.93 mol) of 42.1% by weight of iodine monochloride were dropped into the reaction pot over a period of 2 hours and 20 minutes. After the end of the dropping, the resulting product was aged at 6° C. for 15 minutes. Next, the reaction product was filtered with use of a centrifugal filter, and the cake as a result of the filtration was washed with 110 kg of water. The wet material (composition) thus obtained containing 1,3-diiodo-5,5-dimethylhydantoin had a weight of 15.84 kg. The wet material thus obtained contained 13.55 kg (85.6% by weight) of 1,3-diiodo-5,5-dimethylhydantoin, 1.82 kg (11.5% by weight) of water, 0.22 kg (1.4% by weight) of butyl acetate, and 0.24 kg (1.50% by weight) of elemental iodine.

Example 1

In the same manner as in Experimental Example 1, 32.43 kg of a wet material (containing 85.45% by weight of 1,3-diiodo-5,5-dimethylhydantoin, 11.65% by weight of water (3.78 kg, 209.8 mol), 1.40% by weight of butyl acetate (0.45 kg, 3.9 mol), and 1.50% by weight of elemental iodine (0.49 kg, 1.9 mol)) were obtained. The wet material thus obtained was fed into a conical vacuum dryer having an internal capacity of 200 L. The room temperature was 20° C.

Next, the conical vacuum dryer was rotated, and further reduction of pressure was started. While nitrogen was being introduced at a flow rate of 5.4 L/min (in a gas quantity of 0.111 mol % equivalent/min with respect to a total number of moles of water, butyl acetate, and elemental iodine) into the drying chamber, a rise in temperature was started by passing a heat medium through a jacket of the conical vacuum dryer, so that the temperature in the drying chamber was raised to 50° C. over a period of 3 hours. The rate of temperature rise was 10° C./hour. After that, drying was carried out for 2.5 hours with the temperature in the drying chamber controlled at 50 to 63° C. while the introduction of nitrogen was continued. The total amount of introduction of nitrogen was 1780 L, and was 0.37 mol equivalent with respect to the total number of moles of water, butyl acetate, and elemental iodine. The pressure in the drying chamber during this period was 5.4 kPa to 7.7 kPa. After the end of the drying, the temperature in the drying chamber was lowered to 30° C., and after the reduced pressure was returned to an ordinary pressure with nitrogen, the rotation was stopped.

25.57 kg of a refined product were taken out of the drying chamber. The refined product thus obtained was a pale yellow solid, and contained 98.64% by weight of 1,3-diiodo-5,5-dimethylhydantoin, not greater than 0.2% by weight of elemental iodine, and 1.36% by weight of water. Further, measurement of the refined product by dry sieving showed that particles having a particle size of less than 8 mm occupied 100% of the refined product and the refined product did not contain any particles that have a particle size of not less than 8 mm.

Example 2

In the same manner as in Experimental Example 1, 33.86 kg of a wet material (containing 88.62% by weight of 1,3-diiodo-5,5-dimethylhydantoin, 8.50% by weight of water (2.88 kg, 159.8 mol), 1.38% by weight of butyl acetate (0.47 kg, 4.0 mol), and 1.50% by weight of elemental iodine (0.51 kg, 2.0 mol)) were obtained. The wet material thus obtained was fed into a conical vacuum dryer having an internal capacity of 200 L. The room temperature was 20° C.

Next, the conical vacuum dryer was rotated, and further reduction of pressure was started. While nitrogen was being introduced at a flow rate of 8.1 L/min (in a gas quantity of 0.217 mol % equivalent/min with respect to a total number of moles of water, butyl acetate, and elemental iodine) into the drying chamber, a rise in temperature was started by passing a heat medium through a jacket of the conical vacuum dryer, so that the temperature in the drying chamber was raised to 50° C. over a period of 3 hours. The rate of temperature rise was 10° C./hour. After that, drying was carried out for 4.5 hours with the temperature in the drying chamber controlled at 50 to 60° C. while the introduction of nitrogen was continued. The total amount of introduction of nitrogen was 3650 L, and was 0.98 mol equivalent with respect to the total number of moles of water, butyl acetate, and elemental iodine. The pressure in the drying chamber during this period was 12.7 kPa to 6.6 kPa. After the end of the drying, the temperature in the drying chamber was lowered to 30° C., and after the reduced pressure was returned to an ordinary pressure with nitrogen, the rotation was stopped.

29.11 kg of a refined product were taken out of the drying chamber. The refined product thus obtained was a pale yellow solid, and contained 98.04% by weight of 1,3-diiodo-5,5-dimethylhydantoin, not greater than 0.2% by weight of elemental iodine, and 1.96% by weight of water. Further, measurement of the refined product by dry sieving showed that particles having a particle size of less than 8 mm occupied 100% of the refined product and the refined product did not contain any particles that have a particle size of not less than 8 mm.

Example 3

In the same manner as in Experimental Example 1, 33.66 kg of a wet material (containing 88.95% by weight of 1,3-diiodo-5,5-dimethylhydantoin, 8.60% by weight of water (2.89 kg, 160.4 mol), 0.95% by weight of butyl acetate (0.32 kg, 2.8 mol), and 1.50% by weight of elemental iodine (0.50 kg, 2.0 mol)) were obtained. The wet material thus obtained was fed into a conical vacuum dryer having an internal capacity of 200 L. The room temperature was 20° C.

Next, the conical vacuum dryer was rotated, and further reduction of pressure was started. While nitrogen was being introduced at a flow rate of 10.0 L/min (in a gas quantity of 0.272 mol % equivalent/min with respect to a total number of moles of water, butyl acetate, and elemental iodine) into the drying chamber, a rise in temperature was started by passing a heat medium through a jacket of the conical vacuum dryer, so that the temperature in the drying chamber was raised to 53° C. over a period of 2.5 hours. The rate of temperature rise was 13.2° C./hour. After that, drying was carried out for 6.5 hours with the temperature in the drying chamber controlled at 53 to 55° C. while the introduction of nitrogen was continued. The total amount of introduction of nitrogen was 5400 L, and was 1.46 mol equivalent with respect to the total number of moles of water, butyl acetate, and elemental iodine. The pressure in the drying chamber during this period was 15.7 kPa to 7.4 kPa. After the end of the drying, the temperature in the drying chamber was lowered to 30° C., and after the reduced pressure was returned to an ordinary pressure with nitrogen, the rotation was stopped.

29.11 kg of a refined product were taken out of the drying chamber. The refined product thus obtained was a pale yellow solid, and contained 98.01% by weight of 1,3-diiodo-5,5-dimethylhydantoin, not greater than 0.2% by weight of elemental iodine, and 1.99% by weight of water. Further, measurement of the refined product by dry sieving showed that particles having a particle size of less than 8 mm occupied 100% of the refined product and the refine product did not contain any particles that have a particle size of not less than 8 mm.

Comparative Example 1

In the same manner as in Experimental Example 1, 17.6 kg of a wet material (containing 88.7% by weight of 1,3-diiodo-5,5-dimethylhydantoin) were obtained. The wet material thus obtained was fed into a conical vacuum dryer having an internal capacity of 200 L. The room temperature was 20° C. The conical vacuum dryer was rotated, and further reduction of pressure was started. Without the introduction of the inert gas into the drying chamber, the temperature in the drying chamber was raised from room temperature to 70° C. over a period of 0.5 hours by passing, through the jacket of the conical vacuum dryer, warm water having its temperature controlled at 72° C. to 74° C. After that, the wet material was dried for 9 hours while the temperature in the drying chamber was kept at 70° C. to 74° C. The pressure in the drying chamber during this period was 7 kPa to 8 kPa.

After the end of the drying, the temperature in the drying chamber was lowered to 30° C., and the reduced pressure was returned to an ordinary pressure with nitrogen. Then, the dried product was taken out of the drying chamber. A dark brown solid was found adhering to an area around a manhole inlet of the conical vacuum chamber or on an inner side of a butterfly valve of the conical vacuum dryer. Further, black elemental iodine was also found. Presumably, the black elemental iodine was produced by the decomposition of 1,3-diiodo-5,5-dimethylhydantoin. The dark brown solid was analyzed, and was found to contain 91.1% by weight of 1,3-diiodo-5,5-dimethylhydantoin. Measurement of the dried product by dry sieving showed that particles having a particle size of less than 8 mm, particles having a particle size of 8 to 15 mm, and particles having a particle size of greater than 15 mm occupied 80%, 9%, and 11% of the dried product, respectively.

INDUSTRIAL APPLICABILITY

Since a halohydantoin compound can be used as (i) a sensitizer for a photograph and the like and (ii) a halogenating agent or oxidizing agent that is used in the production of a medicinal product, an agricultural chemical, and a compound, the present invention can be utilized in the fields of photographs, medicinal products, agricultural chemicals, chemical products, etc.

REFERENCE SIGNS LIST

1 Dryer
2a, 2b Collection tank
3 Pressure reducing pump
4a, 4b Duct
5a, 5b Manometer
6 Filter
7 Sight glass

The invention claimed is:

1. A method for drying a halohydantoin compound, comprising the steps of:
   (a) providing, in a dryer, a composition containing (i) at least one component selected from the group consisting of water, an organic solvent, and elemental halogen and (ii) a halohydantoin compound; and
   (b) drying the composition under reduced pressure in the dryer, the reduced pressure being reduced to a pressure lower than atmospheric pressure while introducing an inert gas from an outside source into the dryer, wherein the rate of introduction of the inert gas is not less than 0.01 mol % equivalent/min and not greater than 5.0 mol % equivalent/min, with respect to a total molar quantity of one component selected from the group consisting of water, an organic solvent, and elemental halogen prior to the drying.

2. The method according to claim 1, wherein the temperature in the dryer during the drying is not lower than 15° C. and not higher than 100° C., and a rate of temperature rise is not less than 1° C./hour and not greater than 40° C./hour.

3. The method according to claim 1, wherein the pressure in the dryer during the drying is not lower than 0.1 kPa and not higher than 50 kPa.

4. The method according to claim 1, wherein the organic solvent is at least one selected from the group consisting of an ester solvent, an aromatic solvent, an ether solvent, and a chlorine solvent, each having a boiling point of not lower than 30° C. and not higher than 200° C. under the atmospheric pressure.

5. The method according to claim 1, wherein the elemental halogen is at least one selected from the group consisting of iodine, bromine, and chlorine.

6. The method according to claim 1, wherein the halohydantoin compound is a compound represented by chemical formula I:

[Chem. 1]

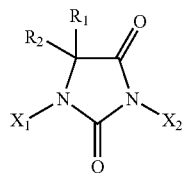
(I)

where
- $R_1$ and $R_2$ are either identical to or different from each other, and are (i) each independently H, a substituted or unsubstituted C1 to C10 aliphatic hydrocarbon radical, a substituted or unsubstituted C3 to C10 alicyclic hydrocarbon radical, or a substituted or unsubstituted C6 to C10 allyl group or aralkyl group, more preferably H or a C1 to C8 aliphatic hydrocarbon radical, or even more preferably H or a methyl group, or (ii) most preferably both methyl groups; and
- $X_1$ and $X_2$ are either identical to or different from each other, and are (i) each independently H or a halogen atom, more preferably H, Br, or I, or even more preferably H or I, or (ii) most preferably both I, excluding a halohydantoin compound wherein $X_1$ and $X_2$ are both H.

* * * * *